United States Patent
Bosch-Tubert et al.

(10) Patent No.: US 12,201,095 B2
(45) Date of Patent: Jan. 21, 2025

(54) ANIMAL MODEL OF MUCOPOLYSACCHARIDOSES TYPE IVA

(71) Applicants: ESTEVE PHARMACEUTICALS, S.A., Barcelona (ES); UNIVERSITAT AUTÓNOMA DE BARCELONA, Cerdanyola del Vallès (ES)

(72) Inventors: Maria-Fátima Bosch-Tubert, Cerdanyola del Vallès (ES); Joan Bertolin-Galvez, Barcelona (ES); Miguel Garcia-Martinez, Terrassa (ES); Victor Sanchez-Clares, Sabadell (ES); Anna-Maria Pujol-Altarriba, Sallent (ES)

(73) Assignees: ESTEVE PHARMACEUTICALS, S.A., Barcelona (ES); UNIVERSITAT AUTÓNOMA DE BARCELONA, Cerdanyola del Vallès (ES)

( * ) Notice: Subject to any disclaimer, the term of this patent is extended or adjusted under 35 U.S.C. 154(b) by 849 days.

(21) Appl. No.: 17/293,653

(22) PCT Filed: Nov. 14, 2019

(86) PCT No.: PCT/EP2019/081303
§ 371 (c)(1),
(2) Date: May 13, 2021

(87) PCT Pub. No.: WO2020/099548
PCT Pub. Date: May 22, 2020

(65) Prior Publication Data
US 2022/0007621 A1     Jan. 13, 2022

(30) Foreign Application Priority Data
Nov. 15, 2018 (EP) .................................... 18382806

(51) Int. Cl.
*A01K 67/0276* (2024.01)
*C12N 15/113* (2010.01)

(52) U.S. Cl.
CPC ........ *A01K 67/0276* (2013.01); *C12N 15/113* (2013.01); *A01K 2217/075* (2013.01); *A01K 2227/105* (2013.01); *A01K 2267/0306* (2013.01)

(58) Field of Classification Search
None
See application file for complete search history.

(56) References Cited

PUBLICATIONS

Fukuda et al. Mucopolysaccharidosis IVA: Submicroscopic deletion of 16q24.3 and a novel R386C mutation of n-acetylgalactosamine-6-sulfate sulfatase gene in a classical Morquio disease. Human Mutation 1996, 7;2:123-134. (Year: 1996).*
Altschul, Stephen, F., et al. , "Basic local alignment search tool", ). Nul. Biol., 215, 1998, pp. 403-410.
Altschul, Stephen, F., et al., "Gapped BLAST and PSI-BLAST: & new generation of protein database search programs", Nucleic Acids Research, vol. 25, No. 17, 1997, pp. 3389-3482.
International Search Report for PCT/EP2019/081303 Dec. 19, 2019.
Morrone, Amelis, et al., "Morquio A syndrome-associated mutations: a review of alterations in the GALNS gene and a new locus-specific database", Human Mutation, vol. 35, No. 13, 2814, pp. 1271-1279.
Rowan, Daniel, J., et al., "Assessment of bone dysplasia by micro-CT and glycosaminoglycan levels in mouse models for sucopolysaccharidosis type I, IIIA, IVA, and VII", J Inherit Metab Dis. , 36(2), Mar. 2013, pp. 235-246.
Tomatsu, Shunji, et al., "Development of MPS IVA mouse (Galns tm(hC795 sC765)slu) tolerant to human N-acetylgalactosamine-6-sulfate sulfatase", Human Molecular Genetics, vol. 14, No. 22, 2005, pp. 3323-3335.
Tomatsu, Shonji, et al., "Enhancement of drug delivery: enzyme-replacement therapy for Murine Morquio A syndrome", www.moleculartherapy.org, vol. 18, No. 6, Jun. 2010, pp. 1094-1102.
Tomatsu, Shonji, et al., "Enzyme replacement therapy for treating mucopolysaccharidosas type IVA (Morquio A syndrome) : effect and limitations", Expert Opinion on Orphan Drugs, 3(11), 2019, pp. 1279-1290.
Tomatse, Shunji, et al., "Enzyme replacement therapy in a murine model of Morquio A syndrome". Human Molecular Genetics, vol. 17, No. 6, 2088, pp. 815-824.
Tomatsu, Shonji, et al., "Morquio A syndrome: diagnosis and current and therapies", Pediatr Endocrinol Rev., 12(0 1), Sep. 2014, pp. 141-151.
Tomatsb, Shunji, et al., "Mouse model of N-acetylgslactosemine-d-sulfate sulfatase deficiency (Gains -/-) produced by targeted disruption of the gone defective in Morquio A disease", Human Molecular Genetics, vol. 12, No. 24, 2003, pp. 3349-3358.
Tomatsu, Shunji, et al., "Murine model (Gains to(C765)slu) of MPS IVA with wissense mutation at the active site cysteine conserved among sulfatase proteins", Molecular Genetics and Metabolism, 91, 2007, pp. 251-258.
Tomatsu, Shuni, et al., "Mutation and polymorphism spectrum of the GALNS gene in mucopolysaccharidosis IVA (Morquio A)", Human Mutation, 26(6), 2005, pp. 500-512.
Van Diggelen, O, P., et al., "A Fluorimotric enzyme sssay for the diagnosis of Morquio disease type A (MPS IVA)", Clinica Chimica Acta, 187, 1998, pp. 131-148.

* cited by examiner

Primary Examiner — Allison M Fox
Assistant Examiner — Qinhua Gu
(74) *Attorney, Agent, or Firm* — HUESCHEN AND SAGE

(57) ABSTRACT

The present invention provides a new animal model for mucopolysaccharidosis type IVA or Morquio A syndrome and to methods of generating the animal model and uses thereof.

8 Claims, 8 Drawing Sheets
Specification includes a Sequence Listing.

A

B

A

B

US 12,201,095 B2

ANIMAL MODEL OF MUCOPOLYSACCHARIDOSES TYPE IVA

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,465 Bytes ASCII (Text) file named "SEQUENCE_LISTING_ESTEVE_82.txt," created on 6 May 2021.

FIELD OF THE INVENTION

The present invention relates to a non-human animal model of mucopolysaccharidoses type IVA or Morquio A syndrome and to methods of generating said animal model and uses thereof. In particular, to the use of said model in the evaluation of therapies for the treatment of this disorder.

BACKGROUND OF THE INVENTION

The lysosome is an organelle found in the cytoplasm of animal cells that contains more than 50 hydrolases that break down biomolecules during the recycling of worn-out cellular components or after the engulfment of viruses and bacteria. This organelle contains several types of hydrolytic enzymes, including proteases, nucleases, glycosidases, lipases, phospholipases, phosphatases and sulfatases. All enzymes are acid hydrolases.

Lysosomal storage diseases (LSDs) are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis.

LSDs are individually rare, although as a group these disorders are relatively common in the general population. The combined prevalence of LSDs is approximately 1 per 5,000 live births. However, some groups within the general population are particularly afflicted by a high occurrence of LSDs. For instance, the prevalence of Gaucher and Tay-Sachs diseases in descendants from Jewish Central and Eastern European (Ashkenazi) individuals is 1 per 600 and 1 per 3,900 births, respectively.

The mucopolysaccharidoses (MPS) are a group of seven LSD diseases characterized by the absence or deficiency of a specific lysosomal enzyme involved in the metabolism of Glucosaminoglycans (GAGs). All MPS have an autosomal recessive pattern of inheritance, with the exception for MPSII (Hunter disease) that has an X chromosomal linked inheritance.

Of the seven MPS, mucopolysaccharidosis type IV (MPSIV or Morquio syndrome) has two sub-types, A and B. Morquio A and B are both autosomal recessive inherited conditions, which affect males and females equally. Morquio A or MPSIVA is a rare condition and existing data on prevalence are scarce and variable. Reported estimates range from 1 per 76,320 in Northern Ireland to 1 per 641,178 in Western Australia. MPSIVA is caused by the deficiency of one of the enzymes involved in the degradation of the GAG Keratan sulfate (KS) and Chondroitin 6-sulfate (C6S). The gene coding this enzyme has been identified and various mutations have been reported.

MPSIVA is caused by the deficiency in the activity of the enzyme galactosamine (N-acetyl)-6-sulfatase (GALNS, EC 3.1.6.4). GALNS is a lysosomal enzyme which hydrolysis the sulfate ester group of N-acetylgalactosamine-6-sulfate at the nonreducing end of chondroitin-6-sulfate (C6S) and that of galactose-6-sulfate at the nonreducing end of keratan sulfate (KS). As a consequence of the sustained accumulation of non-degraded C6S and KS progressive cellular damage occurs, resulting in multisystemic disease. Presently, about 180 different mutations have been identified in the human GALNS gene leading to the deficiency of the activity of the GALNS enzyme.

The majority of KS and C6S are produced by chondrocytes, and therefore, the undegraded substrates accumulate mainly in cells and extracellular matrix of cartilage. This has a direct impact on cartilage and bone development, leading to systemic skeletal dysplasia. In patients with Morquio A, cartilage cells are vacuolated, and this results in abnormal chondrogenesis and/or endochondral ossification. Most of the patients with MPSIVA are born apparently healthy and the symptoms develop progressively. Initial symptoms are recognized between 1 and 3 years of age and mean age at diagnosis is around 4.7 years. The main skeletal features include: striking shot trunk dwarfism, odontoid hypoplasia, pectus carinatum, kyphosis, scoliosis, genu valgum, coxa valga, flaring of the lower ribs, hypermobile joints and abnormal gait with a tendency to fall. Other potential complications include pulmonary compromise, valvular heart disease, hearing loss, hepatomegaly, fine corneal clouding, coarse facial features and widely spaced teeth with abnormally thin enamel and frequent caries. MPSIVA patients preserve intelligence. The rate of disease progression and the phenotypic features present are variable between patients. MPSIVA phenotypes are defined as severe if final height is below 120 cm, as intermediate if final height is above 120 cm and below 140 cm, and as mild if ultimate height is above 140 cm throughout ages. Reported life expectancies ranging from second decade of life to 70 years of age. This variability may be related to multiple factors, such as the nature of the mutation, ethnicity or differences in the health care that the patient receives.

In 2014, recombinant human GALNS commercialized as Elosulfase alfa. VIMIZIN® (BioMarin Pharmaceutical Inc) was approved by the Food and Drug Administration (FDA) and European Medicines Agency (EMA) for the treatment of MPSIVA. This enzyme replacement therapy has been tested in two different mouse models of the disease (Tomatsu et al., 2008, 2010a, 2015).

Three MPSIVA mouse models have been generated: i) a knock-out (KO) mouse by gene deletion, ii) a knock-in mouse expressing inactive human GALNS and iii) a knock-in MPSIVA mouse model with a missense mutation at the active site (Tomatsu et al. 2003, Tomatsu et al. 2005, Tomatsu et al. 2007).

The first homozygous GALNS KO mouse was generated by a disruption in the exon 2 of the Galns gene. This KO mouse had no detectable GALNS activity in peripheral tissues and also show an elevation of urinary KS levels accompanied by an accumulation of KS in various organs, such as brain, liver, spleen or kidney (Tomatsu et al. 2003). Specifically, at 2 months of age, lysosomal storage was detected in sinusoidal lining cells and Kupffer cells of liver and spleen. Twelve-months-old mice did not present vacuolar changes in hepatocytes or in renal tubular epithelial cells. Only cells at the base of heart valves presented vacuolar alterations. In the brain, storage materials were only detected in meningeal cells and in neocortical and hippocampal neurons. Further, an excess of KS and C6S in the cytoplasm of corneal epithelial cells was also observed by immunohistochemistry. Nevertheless, compared to healthy wild-type mice, KO mice had similar survival and showed no obvious skeletal dysplasia, at any age analysed.

Another MPSIVA mouse model was generated by targeted mutagenesis of the Galns gene, by replacement of the endogenous mouse gene by a mutated human GALNS gene. This MPSIVA mouse model was tolerant to human GALNS and it was generated to prevent immune reaction against enzyme replacement therapy (Tomatsu et al. 2005a). This mouse model did not show GALNS activity, however serum KS levels showed no differences compared with wild-type mouse. Accumulation of glycosaminoglycans was only detected in visceral organs, cartilage, bone, cornea, and brain. Similarly to KO mice, lysosomal storage material was detected within the cells of the sinusoidal lining of the spleen and Kupffer cells and also in hepatocytes. At cartilage level, chondrocytes showed lysosomal storage material in the cytoplasm. Lysosomal distention was also detected in bone, specifically in osteocytes and osteoblasts. Despite this lysosomal accumulation, no radiographic differences were detected in legs, spine or ribs between MPSIVA tolerant mice and wild-type mice. Moreover, micro-CT analysis of bone mineral density (BMD) in femur and tibia was not significantly changed between wild-type and MPS IVA mice (WT: 496.24±38.75 mgHA/cc, MPS IVA: 500.73±22.25 mgHA/cc). Although there was an accumulation of glycosaminoglycans in visceral organs and chondrocytes, MPSIVA tolerant mice did not show skeletal dysplasia and presented normal KS levels in blood (Rowan et al. 2013).

The third mouse model for MPSIVA was another knock-in mouse generated by replacing the Cys76 by Ser in the endogenous murine Galns using targeted mutagenesis (Tomatsu, 2007). Homozygous mice had no detectable GALNS enzyme activity and lysosomal storage was already present at 2-4 months of age. No changes were observed in bones despite the visceral storage of GAGS in organs. Therefore, this mouse model displayed a milder phenotype due to the lack of skeletal features of human MPSIVA patients.

Despite the accumulation of undegraded materials in the lysosomes of bone and cartilage, none of these MPSIVA mouse models developed the bone pathology of Morquio A patients.

Thus, new animal models of Morquio A syndrome are needed which mimics the human disease and which can be used to for evaluating the efficacy of a treatment for mucopolysaccharidoses type IVA or Morquio A syndrome.

SUMMARY OF THE INVENTION

The present invention provides animal model for mucopolysaccharidoses type IVA or Morquio A syndrome.

Although in the prior art, other animal models have been shown to display some characteristics associated with Morquio A syndrome, it has not previously been shown that such animals can display all the core characteristics, nor have such animals been considered as models for Morquio A syndrome or other conditions.

Thus, in a first aspect, the present invention refers to a genetically modified non-human animal model of mucopolysaccharidoses type IVA or Morquio A syndrome comprising a missense mutation in the endogenous Galns gene corresponding to the human missense mutation R386C, wherein the Arginine (R) at position 386 of SEQ ID NO: 2 is substituted by Cysteine (C) or a mutation 1156 C>T, wherein the cytosine (C) at position 1156 of SEQ ID NO: 1 is substituted by thymine (T), and wherein said model expresses at least one phenotype associated with mucopolysaccharidoses type IVA or Morquio A syndrome.

In another aspect, the invention refers to a cell line derived from a non-human animal model according to the invention.

A further aspect of the present invention relates to the use of an animal model or a cell line according to the invention for the screening of compounds for the treatment or prevention of mucopolysaccharidoses type IVA or Morquio A syndrome.

Still, a further aspect of the invention relates to a method for determining the effect of a compound on an animal model according to the invention, comprising placing into contact said animal model with said compound and detecting the presence or absence of a physiological, histological or morphological change in said animal as a response to said compound.

In a still further aspect, the invention refers to the use of an animal model according to the invention for evaluating the efficacy of a treatment for mucopolysaccharidoses type IVA or Morquio A syndrome.

In another aspect, the invention relates to a method for evaluating the efficacy of a pharmaceutical composition or compound, said method comprising the steps of
  i) providing the non-human animal model according to the invention; and
  ii) evaluating the effect on said non-human animal model treated with said pharmaceutical composition or compound.

In a further aspect, also encompassed is a method for evaluating the effect of a treatment of mucopolysaccharidoses type IVA or Morquio A syndrome, said method comprising the steps of
  i) providing the non-human animal model according to the invention with a pharmaceutical composition or compound to be tested,
  ii) evaluating the effect observed on said model treated with a pharmaceutical composition or compound.

DEFINITIONS

Figure 1:
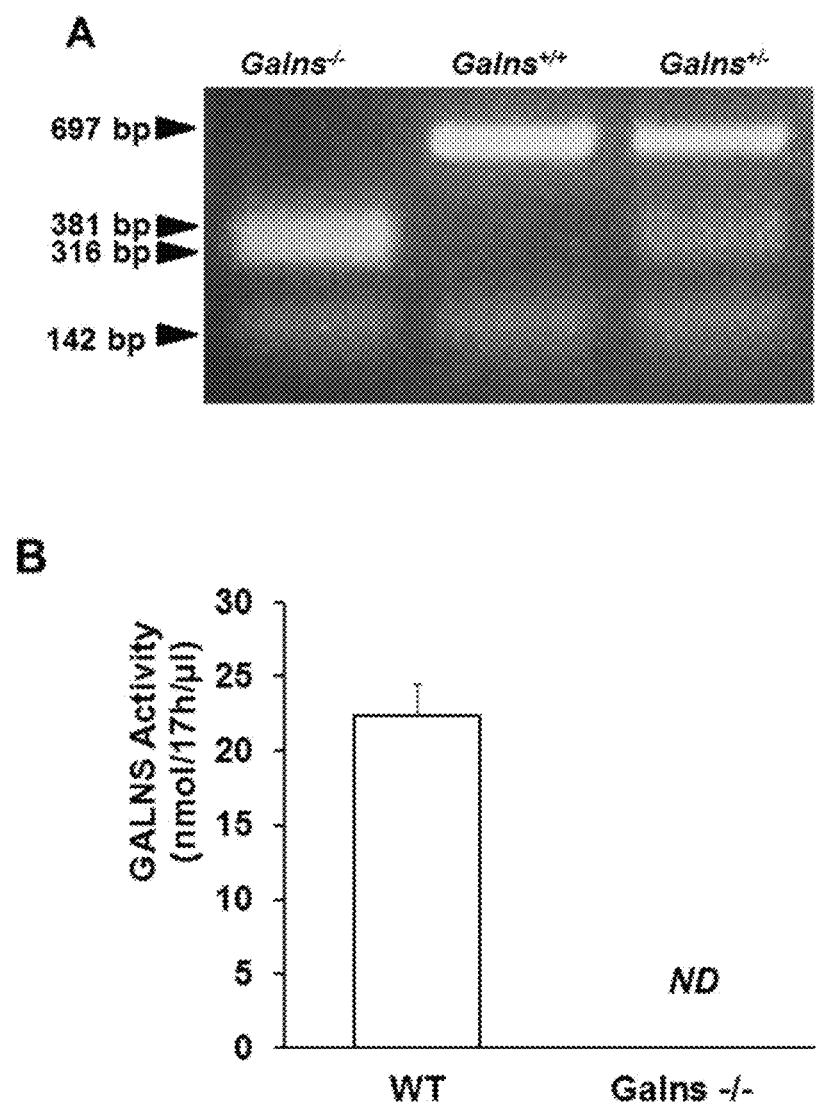
FIG. 1. Genetic and biochemical characterization of Galns$^{-/-}$ rats. (A) Representative image of an agarose gel showing PCR amplicons obtained when genotyping WT (Galns$^{+/+}$), heterozygous (Galns$^{+/-}$) and homozygous (Galns$^{-/-}$) rats after digestion with MboII restriction enzyme. (B) GALNS activity was measured in serum samples of F0 wild-type and Galns$^{-/-}$ male and female rats of 5 months of age. Values are means±SEM of 2-10 rats per group. ND: non-detected.

The terms "nucleotide sequence" or "isolated nucleotide sequence" or "polynucleotide sequence" or "polynucleotide" or "isolated polynucleotide sequence" are interchangeably used herein and refer to a nucleic acid molecule, either DNA or RNA, containing deoxyribonucleotides or ribonucleotides respectively. The nucleic acid may be double stranded, single stranded, or contain portions of both double stranded or single stranded sequence.

By "expression" is meant a process by which polynucleic acids are transcribed into mRNA and translated into peptides, polypeptides, or proteins. If the polynucleic acid is derived from genomic DNA and an appropriate eukaryotic host cell or organism is selected, expression can include splicing of the mRNA. The "nucleic acid" encompasses ribonucleic acid (RNA) or deoxyribonucleic acid (DNA), which DNA can be complementary DNA (cDNA) or genomic DNA.

The terms "% sequence identity", "% identity" or "% sequence homology" refer to the percentage of nucleotides or amino acids of a candidate sequence that are identical to the nucleotides or amino acids in the sequence of reference, after aligning the sequences to achieve the maximum % sequence identity. In a preferred embodiment, sequence identity is calculated based on the full length of two given SEQ ID NO or on part thereof. The % sequence identity can be determined by any methods or algorithms established in the art, such as the ALIGN, BLAST and BLAST 2.0 algorithms. See Altschul S, et al., Nuc Acids Res. 1977; 25:3389-3402 and Altschul S, et al., J Mol Biol. 1990; 215:403-410. Herein, the "% sequence identity", "% identity" or "% sequence homology" is calculated dividing the number of nucleotides or amino acids that are identical after aligning the sequence of reference and the candidate sequence, by the total number of nucleotides or amino acids in the sequence of reference and multiplying the result by 100.

Optionally, in determining the degree of amino acid similarity, the skilled person may also take into account the so-called "conservative" amino acid substitutions, as would be clear to the skilled person. Conservative amino acid substitutions are based on the interchangeability of residues having similar side chains. For example, the group of amino acids having aliphatic side chains includes glycine, alanine, valine, leucine, and isoleucine; the group of amino acids having aliphatic-hydroxyl side chains includes serine and threonine; the group of amino acids having amide-containing side chains includes asparagine and glutamine; the group of amino acids having aromatic side chains includes phenylalanine, tyrosine, and tryptophan; the group of amino acids having basic side chains includes lysine, arginine, and histidine; and the group of amino acids having sulphur-containing side chains includes cysteine and methionine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln to Glu; Met to Leu or Ile; Phe to Met, Leu or Tyr; Ser to Thr; Thr to Ser; Trp to Tyr; Tyr to Trp or Phe; and, Val to Ile or Leu.

The terms "codify" or "coding" refer to the genetic code that determines how a nucleotide sequence is translated into a polypeptide or a protein. The order of the nucleotides in a sequence determines the order of amino acids along a polypeptide or a protein.

The term "protein" refers to a macromolecule composed of one or more linear chains of amino acids or polypeptides. Proteins can suffer post-translational modifications, like the conversion of a cysteine residue to 3-oxoalanine, glycosylation or metal binding. Glycosilation of a protein is the addition of different carbohydrates that are linked covalently to the amino acid chain.

The term "treat" or "treatment", as used herein, refers to the administration of a compound or composition to control the progression of a disease. Control of disease progression is understood as the achievement of the beneficial or desired clinical results that include, but are not limited to, reduction of the symptoms, reduction of the duration of the disease, stabilization of pathological states (specifically to avoid additional deterioration), delay of the progression of the disease, improvement in the pathological state, and remission (both partial and total). The control of progression of the disease also involves an extension of survival, compared with the expected survival if treatment is not applied.

The term "effective amount" refers to an amount of a substance sufficient to achieve the intended purpose. A "therapeutically effective amount" to treat a disease or disorder is an amount sufficient to reduce or eradicate the signals and symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "individual" refers to a mammal, preferably human or non-human mammal, more preferably mouse, rat, other rodents, rabbit, dog, cat, pig, cow, horse or primate, further more preferably human.

Unless defined otherwise, all technical and scientific terms used herein have the same meaning as commonly understood by one of ordinary skill in the art to which this invention belongs.

As used herein and in the appended claims, the singular forms "a", "and", and "the" include plural referents unless the context clearly dictates otherwise. Thus, for example, reference to "a peptide" also includes a plurality of such peptides.

DETAILED DESCRIPTION OF THE INVENTION

MPSIVA is caused by the deficiency in the activity of the enzyme galactosamine (N-acetyl)-6-sulfatase (GALNS). GALNS is a lysosomal enzyme which hydrolyses the sulfate ester group of N-acetylgalactosamine-6-sulfate at the non-reducing end of chondroitin-6-sulfate (C6S) and that of galactose-6-sulfate at the non-reducing end of keratan sulfate (KS). As a consequence of the sustained accumulation of non-degraded C6S and KS, progressive cellular damage occurs, resulting in multisystemic disease.

As mentioned before, none of the MPSIVA animal models described up to date develops the bone pathology of Morquio A patients. Thus, a new animal model of Morquio A syndrome which mimics the human disease and which can be used for evaluating the efficacy of a treatment for mucopolysaccharidoses type IVA or Morquio A syndrome is needed.

The present invention provides a new non-human animal model of mucopolysaccharidoses, in particular mucopolysaccharidoses type IVA or Morquio A syndrome. Indeed, the inventors have found a new animal model of Morquio A syndrome which reproduces the core sings of the human disease.

The gene for galactosamine (N-acetyl)-6-sulfatase, GALNS, in humans is located on chromosome 16q24.3 and has 14 exons. The GALNS cDNA has an open reading frame of 1566 bp which encodes a 522 amino acid protein. About 140 different mutations have been described, and approximately 70% of these are missense mutations. Genotype/phenotype correlation exists for some of these mutations. The term "missense mutation" as used herein refers to a change in one amino acid in a protein, which arise from a point mutation in a single nucleotide.

Figure 7:
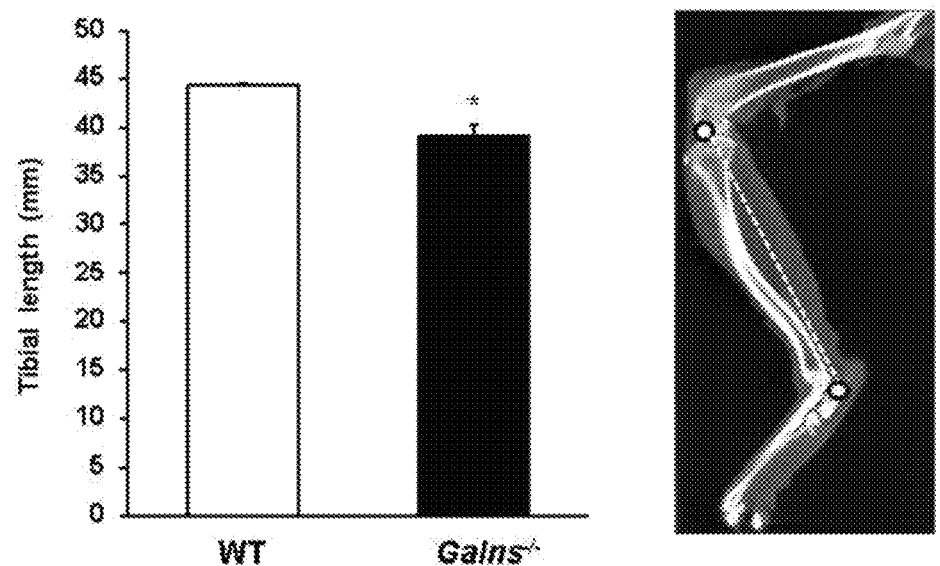
FIG. 7. Micro-computed tomography (μCT) analysis of 3-month-old male rats. (A) Quantification of tibia length from medial condyle to medial malleolus in WT and Galns$^{-/-}$ rats. Values are means±SEM of 3-4 rats per group. *P<0.05 vs. Galns$^{+/+}$ rats. (B) Representative μCT images of coronal sections from the head of WT and Galns$^{-/-}$ rats showing altered mandibular bones (arrowheads) in Galns$^{-/-}$ compared to WT jaws.
Figure 7:
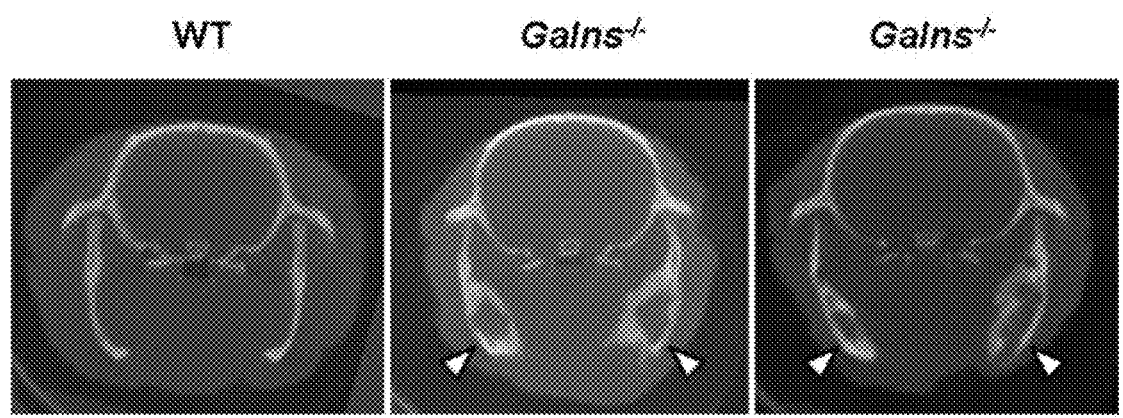
Figure 8:
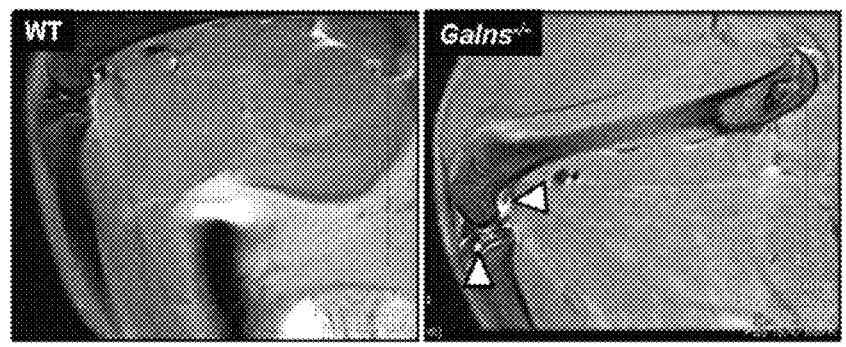
FIG. 8. Morphological and histological analysis of MPSIVA rat bones. Osteoarthritis signs in MPSIVA rats analysed by Magnetic resonance imaging (MRI). Representative sagittal (A) and coronal (B) sections of knees from 6-month-old WT and Galns$^{-/-}$ rats evidencing the pathological presence of fluids marked with arrowheads in the head of tibia from MPSIVA animals. (C) Representative images of a haematoxylin-eosin stain in tibia sections showing loss of articular cartilage and enlarged chondrocytes in 8-month-old homozygous MPSIVA rats.
Figure 8:
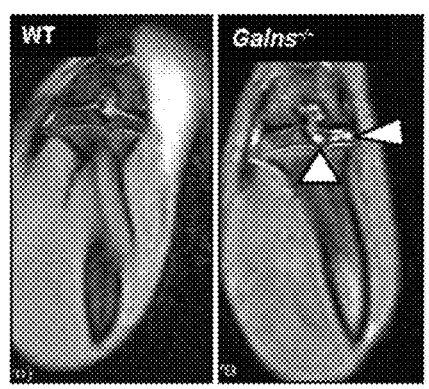
Figure 8:
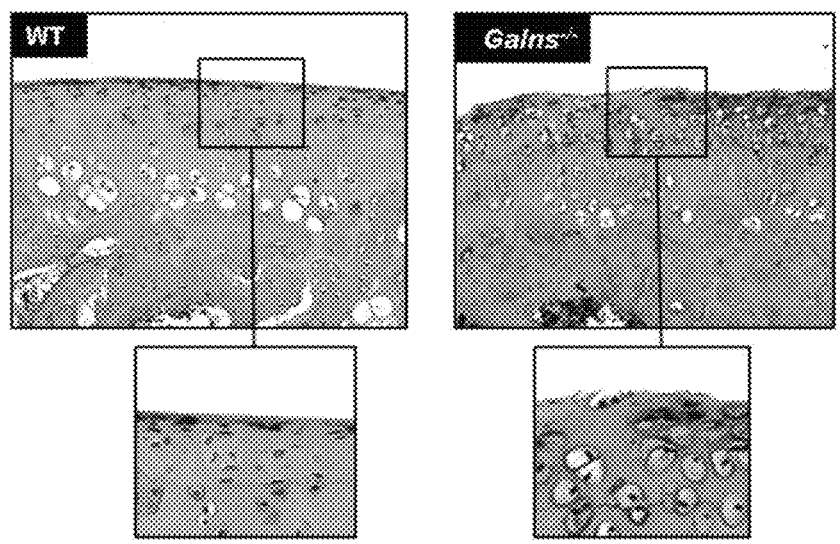

The animal model of the present invention comprises a missense mutation in the endogenous Galns gene. As shown in the Examples accompanying the present invention, Galns$^{-/-}$ animals comprising a missense mutation in the endogenous Galns gene corresponding to the human missense mutation R386C, in which the Arginine (R) at position 386 of SEQ ID NO: 2 is substituted by Cysteine (C) or a mutation 1156 C>T wherein the cytosine (C) at position 1156 of SEQ ID NO: 1 is substituted by thymine (T), showed a significant reduction in tibia length compared to wild-type animals (FIG. 7). Bone alterations were also detected (FIGS. 7 and 8). Indeed, the results confirmed alteration of chondrocytes, which led to abnormal articular cartilage, which finally resulted in osteoarthritis development. Similar alterations are found in human MPSIVA patients. Moreover, the alteration in tibial condyles may be consistent with the genu valgum sign, a MPSIVA clinical feature in humans characterized by the knees angle in and touch each other when the legs are straightened.

Thus, in a first aspect, the present invention relates to a genetically modified non-human animal model of mucopolysaccharidoses type IVA or Morquio A syndrome comprising a missense mutation in the endogenous Galns gene corresponding to the human missense mutation R386C in which the 386th Arginine (R) of SEQ ID NO: 2 is substituted by Cysteine (C) or a mutation 1156 C>T characterized by substitution of cytosine (C) for thymine (T) at position 1156 of SEQ ID NO: 1, wherein said model expresses at least one phenotype associated with mucopolysaccharidoses type IVA or Morquio A syndrome.

As shown in the Examples below, in order to determine the position of the corresponding Galns mutation (1156 C>T) in a non-human animal, the human GALNS protein sequence (SEQ ID NO: 2) is aligned with the non-human animal GALNS protein sequence, for example, the Rattus norvegicus GALNS protein sequence (SEQ ID NO: 4). Thus, in a first approach, the position of the human R386 in the non-human animal protein is identified. The equivalent amino acid, in particular, the Arginine 386, in the non-human animal, in particular in the rat protein, is then determined. As an example, the Arginine amino acid in the rat model shown below was located in position 388 (R388C). Further, the equivalent nucleotide to the human C>T located in position 1156 (SEQ ID NO: 1) was determined by sequence alignment techniques. As shown in the Examples, said nucleotide is located in the position 1162 of the rat GALNS coding sequence (SEQ ID NO: 3).

In a preferred embodiment, the non-human animal model of the invention is an animal that has been genetically modified, so that a missense mutation has been introduced in the endogenous Galns gene. According to the present invention, said mutation corresponds to the human missense mutation R386C in which the 386th Arginine (R) of SEQ ID NO: 2 is substituted by Cysteine (C), which arise from a point mutation 1156 C>T characterized by substitution of cytosine (C) for thymine (T) at position 1156 in a nucleotide sequence as set forth in SEQ ID NO: 1.

In a more particular embodiment of the invention, said missense mutation is characterized by a substitution of cytosine (C) for thymine (T) at position 1162 in the endogenous Galns gene (1162 C>T) in a nucleotide sequence as set forth in SEQ ID NO: 3 or a mutation in the amino acid sequence as set forth in SEQ ID NO: 4 consisting of a substitution of Arginine (R) for Cysteine (C) at position 388 (R388C).

The 1162 C>T missense mutation in the endogenous Galns gene means a substitution of cytosine (C) for thymine (T) at position 1162 in a nucleotide sequence as set forth in SEQ ID NO: 3, that leads to an Arginine (R) for Cysteine (C) change at position 388 of SEQ ID NO: 4. In a particular embodiment, said mutation corresponds to the 1156 C>T mutation in human GALNS gene, which is a substitution of cytosine (C) for thymine (T) at position 1156 in a nucleotide sequence as set forth in SEQ ID NO: 1.

The term "non-human animal" as used herein includes a non-human vertebrate animal, and more preferably a mammal, such as a domesticated farm animal (e.g., cow, horse, pig), pet (e.g., dog, cat), or rodent. The terms "rodent" or "rodents" refers to any and all members of the phylogenetic order Rodentia (e.g., mice, rats, squirrels, beavers, woodchucks, gophers, voles, marmots, hamsters, guinea pigs, and agouti) including any and all progeny of all future generations derived therefrom. In a particular embodiment of the invention, the animal is a rodent, more preferably, the animal is a rat.

The term "non-human animal model" as used herein refers to a non-human animal as described above having or displaying the characteristics of a disease or condition. The use as an animal model means any use of an animal to study the disease or condition, such as the use to study the progression or development or the response to new or existing treatments.

As mentioned above, none of the MPSIVA mouse models described in the prior art develop the bone pathology of Morquio A human patients. Thus, although histological signs of storage of chondroitin-6-sulfate (C6S) and keratan sulfate (KS) were evident in the Morquio A mouse models described in the prior art, the animals did not display a dysostosis phenotype, which is characteristic in human patients.

In another particular embodiment, the invention refers to the non-human animal model according to the invention wherein said model expresses at least one phenotype associated with mucopolysaccharidoses type IVA or Morquio A syndrome, wherein said at least one phenotype is dysostosis multiplex.

The term "dysostosis", "dysostosis multiplex" "skeletal dysplasia" or "osteochondrodysplasia" as used herein refers to disorders characterized by abnormalities of cartilage and bone growth, resulting in abnormal shape and size of the skeleton and disproportion of the long bones, spine, and head.

According to the present invention, the animal model of the invention displays a phenotype showing the bone pathology of Morquio A patients, displaying abnormalities in bone growth. In particular, as shown in the Examples accompanying the present invention, the animal model of the invention displays a reduced body length compared to wild-type animals. Body length can be easily measured by, for example, measuring animal's naso-anal length. Also, as shown in the Examples, bone length in the animal model of the invention is reduced compared to wild type animals. Bone length, such as tibia length, can be measured as shown in the Examples below. Thus, in a particular embodiment of the invention, said dysostosis multiplex phenotype comprises reduced body length and/or bone length compared to wild-type animals.

In a more particular embodiment of the invention, said animal model additionally exhibits a phenotype selected from osteoarthritis, thin tooth enamel, dental fragility, malocclusion, corneal clouding, hearing impairment, otitis media, valvular heart disease, respiratory compromise, hepatosplenomegaly and combinations thereof.

The present invention relates to a non-human animal that expresses a non-functional GALNS protein or a GALNS protein that has reduced activity in one or more tissues, as compared to wild-type GALNS protein. Non-functional or reduced activity refers to the GALNS inability to hydrolyse the sulfate ester group of N-acetylgalactosamine-6-sulfate at the non-reducing end of chondroitin-6-sulfate (C6S) and that of galactose-6-sulfate at the non-reducing end of keratan sulfate (KS). As a consequence, a sustained accumulation of non-degraded C6S and KS occurs, resulting in multisystemic disease.

Figure 2:
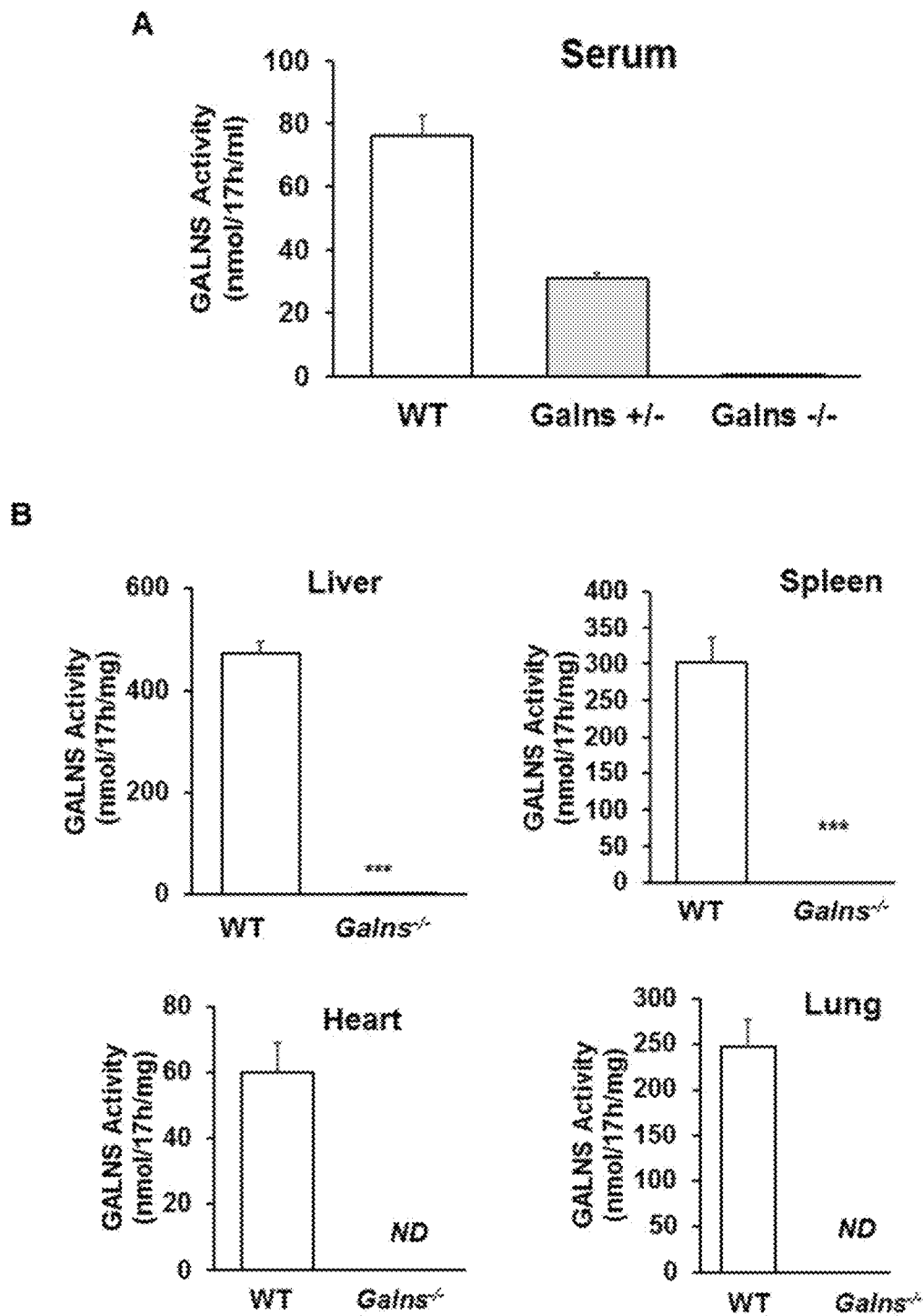
FIG. 2. Determination of GALNS activity in MPSIVA rats after three backcrosses (F4 generation). (A) GALNS activity levels were determined in serum samples of 1-month-old WT, heterozygous (Galns$^{+/-}$) and homozygous (Galns$^{-/-}$) rats. (B) GALNS activity levels in the liver, spleen, heart and lung of 1-month-old WT and Galns$^{-/-}$ male rats. Values are means±SEM of 4-5 rats per group. ***P<0.001 vs. Galns$^{+/+}$ rats. ND: non-detected.
Figure 3:
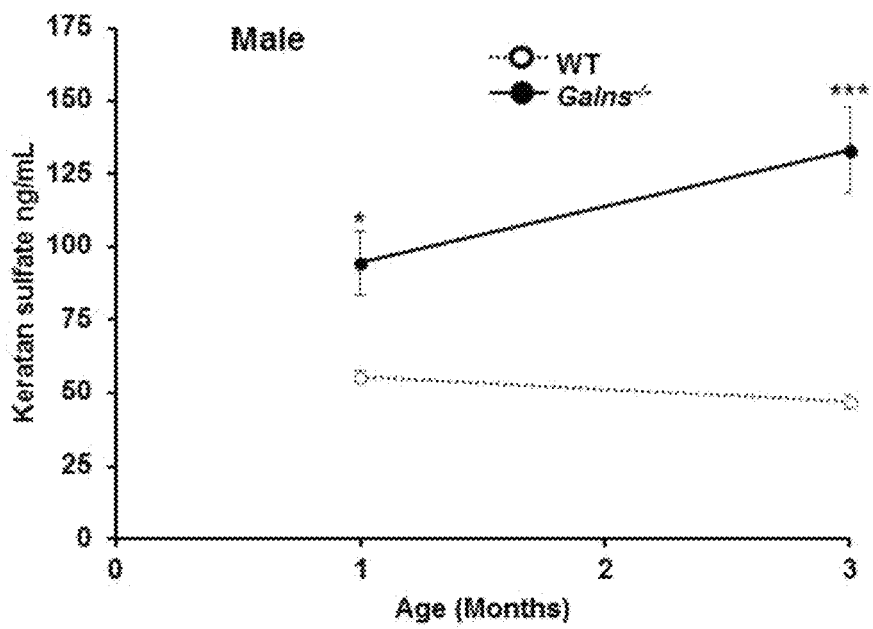
FIG. 3. Quantification of keratan sulfate (KS) levels in serum samples from male (A) and female (B) rats by liquid chromatography-mass spectrometry (LC-MS/MS). Values are means±SEM of 4-5 rats per group. *P<0.05, P<0.01, *P<0.001, vs. male and female Galns$^{+/+}$ rats.
Figure 3:
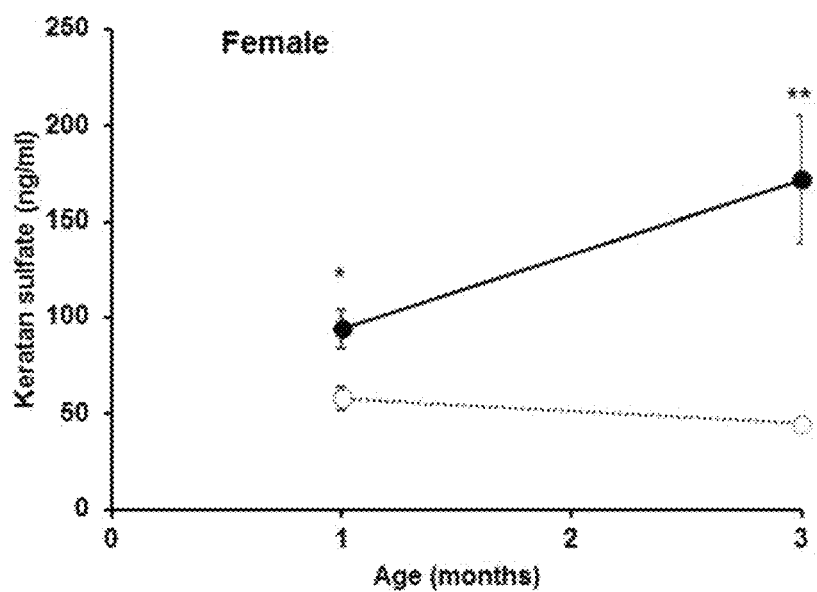

GALNS can be mutated, truncated or otherwise rendered non-functional. In an embodiment, the amino acid expressed by the Galns knock-in mouse model of the present invention includes sequence SEQ ID NO: 4, which corresponds to GALNS amino acid sequence in which Arginine at position 388 is mutated to Cysteine such that the mutated form of GALNS protein has reduced activity in one or more tissues, as compared to wild-type GALNS protein. As it is shown in the Examples accompanying the present invention, homozygous Galns$^{-/-}$ rats did not show GALNS activity (FIG. 2A). Moreover, the Galns$^{-/-}$ rats did not present detectable GALNS activity in peripheral tissues, such as liver, spleen, heart or lung (FIG. 2B). Also, a progressive increase in KS levels can be detected in serum samples from MPSIVA rats at different ages (FIGS. 3A and 3B).

In another embodiment, the animal model can express human GALNS that is mutated, in the same fashion as the animal Galns.

The non-human animal encompassed by the present invention includes variants of the above GALNS polypeptides and DNA molecules. A polypeptide "variant", as used herein, is a polypeptide that differs from the recited polypeptide only in substitutions and/or modifications, such that the GALNS inability to hydrolysis the sulfate ester group of N-acetylgalactosamine-6-sulfate at the nonreducing end of chondroitin-6-sulfate (C6S) and that of galactose-6-sulfate at the nonreducing end of keratan sulfate (KS) is retained. Variants can also, or alternatively, contain other modifications, including the deletion or addition of amino acids that have minimal influence on GALNS functional properties.

The present invention encompasses animals that express GALNS polypeptides, variants thereof, or those having amino acid sequences analogous to the amino acid sequences described herein. Such polypeptides are defined herein as GALNS analogs (e.g., homologues), or mutants or derivatives. "Analogous" or "homologous" amino acid sequences refer to amino acid sequences with sufficient identity to the GALNS sequences. For example, an analog polypeptide can be produced with "silent" changes in the amino acid sequence wherein one, or more, amino acid residues differ from the amino acid residues of any one of the GALNS protein, yet still possesses the functional properties of the GALNS. Examples of such differences include additions, truncations, deletions or substitutions of residues of the amino acid sequence of GALNS.

The non-human animal models of the present invention can be made in any non-human animal type. Animals suitable for such experiments can be obtained from standard commercial sources. These include animals such as mice and rats, as well as larger animals such as pigs, cows, sheep, goats, guinea pigs, poultry, emus, ostrichs, cows, sheep, rabbits and other animals that have been genetically engineered using techniques known to those skilled in the art.

As an example, the non-human animal of the invention can be obtained by a process comprising the insertion of a mutation in the GALNS gene in a cell genome. In a specific embodiment, said mutation is introduced by homologous recombination in an endogenous GALNS gene present in the genome of a suitable cell, such as a differentiated cell that normally expresses said gene or an embryonic stem (ES) pluripotent cell, by introducing a homologous recombination vector in said cell which can be used to generate the non-human animal of the invention as described herein.

In a particular embodiment, the non-human animal of the invention is generated using Clustered Regularly Interspaced Short Palindromic Repeats and CRISPR-associated protein 9 (Cas9) technology, hereinafter referred to as CRISPR/Cas9 technology. The term "Cas9" refers to an RNA-guide DNA endonuclease enzyme associated with the CRISPR adaptive immunity, system of some bacteria. Cas9 uses base pairing to recognize and cleave target DNAs with complementarity to the guide RNA (gRNA). The programmable sequence specificity of Cas9 has been harnessed for genome editing and gene expression control m many organisms.

Briefly, a small piece of RNA is created with a short "guide" sequence (gRNA) that binds to a specific target sequence of DNA in a genome. The RNA also binds to the Cas9 enzyme. The modified RNA is used to recognize the DNA sequence, and the Cas9 enzyme cuts the DNA at the targeted location. Although Cas9 is the enzyme most often used, other enzymes, for example Cpf1, can also be used.

Once the DNA is cut, the cell's own DNA repair machinery add or delete pieces of genetic material, or make changes to the DNA by replacing an existing segment with a customized DNA sequence.

In a particular embodiment of the present invention, two specific RNA guides are designed to target the specific DNA site and to drive the Cas9 double strand break close to the genomic site of interest. Also, a single strand donor DNA sequence can be designed to introduce both, the mutation of interest and a new restriction site, useful for genotyping analysis of offspring animals. Two homology arms can also be included in the donor DNA to enable homologous recombination with the Galns genomic sequence. The specific gRNA, the donor DNA, and the Cas9 mRNA are then microinjected into one-cell embryos in order to introduce the mutation of interest into the animal's Galns gene. After Cas9 double strand break and homologous recombination with the donor DNA, the missense mutation is introduced in animal's Galns gene.

In a preferred embodiment, the mutation of interest to be introduced into animal's Galns gene is a mutation that corresponds to the human missense mutation R386C in which the 386th Arginine (R) of SEQ ID NO: 2 is substituted by Cysteine (C), which arises form a point mutation characterized by substitution of cytosine (C) for thymine (T) at position 1156 in a nucleotide sequence as set forth in SEQ ID NO: 1 (1156 C>T). More particularly, said mutation is characterized by a substitution of cytosine (C) for thymine (T) at position 1162 in the endogenous Galns gene in a nucleotide sequence as set forth in SEQ ID NO: 3 (1162 C>T) or a mutation in the amino acid sequence as set forth in SEQ ID NO: 4 consisting of a substitution of arginine (R) for cysteine (C) at position 388 (R388C).

In a more particular embodiment of the invention, said donor DNA is as represented in SEQ ID NO: 7. Said DNA contains a left and a right homology arms, a gRNA target sequence, and contains the missense mutation of interest, in particular C>T missense mutation at position 66 of SEQ ID NO: 7.

The offspring of the non-human animal according to the invention constitutes an additional aspect of the present invention. The offspring of the non-human animal of the invention can be obtained by conventional methods, such as, for example, by classical crossing techniques between the non-human animals of the invention or, alternatively, by in vitro fertilization of ova and/or sperm of the non-human animal of the invention. As used herein the term "offspring" refers to each and every offspring of each generation after the originally transformed non-human animals.

The non-human animal of the invention can be used for in vivo trials. Additionally, the non-human animal of the invention can be used as a source of somatic, foetal or embryonic cells, which once isolated and cultured can be used in in vitro tests. In addition, if desired, it is possible to prepare immortalized cell lines from said cells using conventional techniques. Thus, in another aspect, the invention provides an isolated cell line derived from the non-human animal of the invention. In a specific embodiment, the cell line provided by this invention is a murine cell line comprising a missense mutation in the Galns endogenous gene, more particularly comprising the 1162 C>T missense mutation in the axon 11 of the endogenous Galns gene (SEQ ID NO: 3).

In another aspect, the invention relates to cells isolated from said non-human animal, which can be propagated and optionally immortalized. These cells can be heterozigotes, i.e. containing one mutant allele and one wild type allele for the Galns mutant gene, or homozygotes, i.e. containing two mutant alleles for the Galns gene.

The present invention also provides a method for screening of compounds for the treatment or prevention of Morquio A syndrome. In this regard, the non-human animal model according to the invention or the cell line according to the invention can be used for screening of compounds for the treatment or prevention of Morquio A syndrome.

Thus, in another embodiment, the invention refers to the use of an animal model according to the invention or a cell line according to the invention for the screening of compounds for the treatment or prevention of mucopolysaccharidoses type IVA or Morquio A syndrome.

The candidate compound or drug used in the methods of the invention can include all different types of organic or inorganic molecules, including peptides, oligo- or polysaccharides, fatty acids, steroids, and the like. Also, possible compounds to be screened include, for example, hematopoietic stem cells, enzymes such as, for example, elosulfase alfa, and gene therapy products, such as recombinant vectors, etc. The compounds can be administered singly or in combination with each other.

The invention also provides a method for identifying a compound that affects Morquio A syndrome comprising administering a test compound to a non-human animal model according to the invention and determining the effects on the animal. The present invention includes compounds which prevent, treat, or alter progression of disease which can be screened using this animal model.

The candidate compound can be administered before, during or after a specific disease phenotype appears. Symptoms of disease progression or regression can be monitored using diagnostic tests known for the skilled person in the art. As an example, symptoms of Morquio A syndrome progression or regression include measurement of body or bone length, assessment of dental alterations such as enamel deficiency, dental fragility and malocclusion. Also, for example, morphological and histological changes in bones, such as osteoarthritis signs can be determined by Magnetic Resonance Imaging (MRI). Similarly, markers for disease progression can be monitored by assaying blood, plasma, urine or any accessible fluid. As an example, levels of keratan sulfate (KS) can be measured in serum as an indicator of disease progression as shown in the Examples of the present invention.

Methods for determining the effect of a compound on an animal model according the invention are also included in the context of the present invention. Said method comprises placing into contact said animal model with said compound and detecting the presence or absence of a physiological, histological or morphological change in said animal as a response to said compound. Methods for determining a physiological, histological or morphological change in an animal are well known for the skilled person in the art. Examples of said methods include, magnetic resonance imaging (MRI), used, for example, for analyzing bone osteoarthritis as shown in the Examples below, liquid chromatography-mass spectrometry (LC-MS) for quantification of KS levels in liquid samples, etc.

Thus, in another embodiment, the invention relates to a method for evaluating the effect of a treatment of mucopolysaccharidoses type IVA or Morquio A syndrome, said method comprising the steps of
  i) providing the non-human animal model according to the invention with a pharmaceutical composition or compound to be tested,
  ii) evaluating the effect observed on said model treated with a pharmaceutical composition or compound.

According to a preferred embodiment of the invention, said effect to be observed refers to a physiological change. Said physiological change to be detected in the animal model of the invention refers to any improvement of the physiological alterations present in the animal model as described before, such as, for example, detecting increased levels of GALNS activity in serum or peripheral tissues, such as liver, spleen, heart or lung, after therapy compared to a control (non-treated animal) and/or detecting decreasing levels of keratan sulphate (KS) or chondroitin-6-sulfate (C6S) in serum samples compared to a non-treated animal.

In another embodiment, the invention refers to the use of an animal model according to the invention for evaluating the efficacy of a treatment for mucopolysaccharidoses type IVA or Morquio A syndrome.

In another particular embodiment, the invention refers to a method for screening the efficacy of a pharmaceutical composition or compound, said method comprising the steps of
  i) providing the non-human animal model according to the invention; and
  ii) evaluating the effect on said non-human animal model treated with said pharmaceutical composition or compound.

Compounds of the present invention are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compounds may be administered in liposomes or microspheres (or microparticles). Methods for preparing liposomes and microspheres for administration to a patient are known to those skilled in the art. Essentially, the material is dissolved in an aqueous solution, the appropriate phospholipids and lipids added, along with surfactants if required, and the material dialyzed or sonicated, as necessary. Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months.

The method of the invention is preferably for identifying a compound that reduces the symptoms or signs of such condition.

A method in alternative to that of the invention could comprise administering a test compound to a non-human animal model of the invention and monitoring behavior.

The present invention is illustrated below with the aid of examples. These illustrations are given solely by way of example and do not limit the general spirit of the present invention.

General Procedures

1. Generation of MPS IVA Rats

MPS IVA rats were generated using CRISPR/Cas9 technology. The gRNA, donor DNA, and Cas9 mRNA were pronuclear microinjected in one-cell rat embryos. After Cas9 double strand break and homologous recombination with the donor DNA, the 1162 C>T missense mutation was introduced in the axon 11 of the rat Galns gene.

Rats were weighted weekly after weaning till 6 months of age.

2 Rat Genotyping

Common forward (SEQ ID NO: 8) and reverse (SEQ ID NO: 9) primers were used for genotyping of the genetic engineered rats. PCR reaction generated a 915 bp amplicon that was further digested with MboII restriction enzyme. MboII digestion generated 3 fragments of 697, 142 and 76 bp in the WT allele; and 381, 316, 142 and 76 bp in the MPSIVA allele. Sanger sequencing was done from PCR amplicons using the same primers. Sanger amplicons were aligned with the wild type Galns sequence to detect the MPSIVA allele. TIDE web tool was used to further confirm the presence of the 1162 C>T mutation and the new MboII restriction site in MPSIVA rats.

3. Sample Collection

At sacrifice, animals were deeply anesthetized and then transcardially perfused with 100 ml of PBS to completely clear blood from tissues. Several somatic tissues (including liver, spleen, lung, heart and bones) were collected and either frozen in liquid nitrogen and stored at −80° C. or immersed in formalin for subsequent histological analyses.

4. Galactosamine (N-acetyl)-6-sulfatase (GALNS) Activity and Keratan Sulfate Quantification Liver tissue samples were sonicated in Mili-Q water and femur samples were homogenized in homogenization buffer consisting of 25 mmol/l Tris-HCl, pH 7.2, and 1 mmol/l phenylmethylsulfonyl fluoride. Galactosamine (N-acetyl)-6-sulfatase (GALNS) activity was determined with a 4-methylumbelliferone-derived fluorogenic substrate (Toronto Rerearch Chemicals Inc, Ontario, Canada), as described previously (van Diggelen et al., 1990). Liver, spleen, heart and lung GALNS activity levels were normalized against the total amount of protein, quantified using Bradford protein assay (Bio-Rad, Hercules, CA, US).

Keratan sulfate (KS) levels were determined by liquid chromatography-mass spectrometry (LC-MS/MS) in serum samples.

5. Histological Analysis

Femur and tibia were fixed for 12-24 h in neutral buffered formalin (10%), decalcified weekly with ethylenediaminetetracetic acid (EDTA), embedded in paraffin and sectioned. Bone sections were stained with hematoxilin and eosin to analyse structural changes in articular cartilage.

6. Bone Analysis

Bone volume and architecture were evaluated by Micro-computed tomography (μCT). Mouse tibiae were fixed in neutral buffered formalin (10%) and scanned using the eXplore Locus CT scanner (General Electric) at 27-micron resolution. Bone parameters were calculated with the MicroView 3D Image Viewer & Analysis Tool. The length of the tibia was measured from the medial condyle to medial malleolus.

7. Magnetic Resonance Imaging (MRI) Analysis

In vivo 1H-magnetic resonance imaging (MRI) studies were performed using a 7 T Bruker BioSpec 70/30 USR (Bruker BioSpin GmbH, Ettlingen, Germany) system equipped with a mini-imaging gradient set (400 mT/m) and using a quadrature transceiver volume coil with 72 mm inner diameter. Rats were positioned (supine) in a bed, which allowed delivery of anesthesia (isoflurane, 2.0-3.0% in O2 at 1 L/min), with an integrated heat water circuit for body temperature regulation. Low resolution T2-weighted fast spin-echo images were initially obtained in axial, sagittal and coronal planes to be used as reference scout images. High resolution T2-weighted fast spin-echo images were acquired afterwards in sagittal and coronal planes through the knees.

8. Statistical Analysis

All results are expressed as mean±SEM. Statistical comparisons were made using one-way ANOVA. Multiple comparisons between control and treatment groups were made using Dunnett's post-test, and between all groups using Tukey's post-test. Statistical significance was considered if $P<0.05$, The Kaplan-Meier method was used to analyse survival, and the log-rank test was used for comparisons.

EXAMPLES

Example 1: Human and Rat cDNA Alignment

The human mutation 1156 C>T (SEQ ID NO: 1) that leads to an Arginine-Cysteine amino acid change (R386C) (SEQ ID NO: 2) in the active site (Tomatsu, 2005) was introduced in the rat genome. To this end, the human GALNS protein sequence (SEQ ID NO: 2) was aligned with the Rattus norvegicus GALNS protein sequence (SEQ ID NO: 4) to identify the position of the human R386 in the rat protein. In human Morquio A patients the amino acid change is Arginine for Cysteine in position 386 (R386C). The equivalent arginine amino acid was located in position 388 in the rat protein (R388C). In the human GALNS coding sequence, the C>T single nucleotide change was located in position 1156 (SEQ ID NO: 1). The equivalent C was located in the position 1162 of the rat GALNS coding sequence (SEQ ID NO: 3), located in the exon 11 of rat Galns gene.

Example 2: Generation of MPSIVA Rat Model

A rat model for mucopolysaccharidosis type IVA, containing the point mutation described above has been generated using CRISPR/Cas9 technology.

The 1162 C>T mutation was introduced in exon 11 of the rat Galns gene, generating an arginine-cysteine amino acid change (R388C) in the active site. Two specific RNA guides:

```
gRNA1:
                            (SEQ ID NO: 5)
CCCATATTTTATTACCGTGGCA
and gRNA2:
                            (SEQ ID NO: 6)
TACCGTGGCAACACACTGATGG
``` were designed to target exon 11 and to drive the Cas9 double strand break close to the 1162 C>T genomic site. A single strand donor DNA sequence (SEQ ID NO: 7) was designed to introduce both the 1162 C>T missense mutation and a new MboII restriction site, useful for genotyping analysis of offspring animals. Two homology arms were also included in the donor DNA to enable homologous recombination with the Galns genomic sequence. The specific gRNA, the donor DNA, and the Cas9 mRNA were microinjected into one-cell embryos with the aim of introduce the 1162 C>T missense mutation in the axon 11 of the rat Galns gene.

Example 3: Genotyping and Biochemical Analysis of CRISPR/Cas9 Edited Rats

The first rat generation (F0) that were born after embryo microinjection were genotyped by PCR analysis using specific primers located in the flanking sequences of the 1162 C>T missense mutation site. Next, the PCR product was digested with MboII, leading to different patters depending on the rat genotype (FIG. 1A). Moreover, the PCR product was also analysed by Sanger sequencing to further confirm the presence of the 1162 C>T missense mutation. Sanger amplicons (SEQ ID NO: 10 and SEQ ID NO: 11) were aligned against Rattus norvegicus Galns gene, showing the presence of the 1162 C>T missense mutation and the MboII restriction site in F0 homozygous MPS IVA rats.

Homozygous MPSIVA F0 rats showed no detectable levels of GALNS activity in serum samples compared with wild type counterparts (FIG. 1B), confirming that the introduced mutation led to complete deficiency in the enzyme activity, similarly to that observed in human patients.

Example 4: Selective Backcrosses to Achieve 99% of Off-Target Segregation

The F0 rats that presented the C>T mutation were crossed with wild-type rats to segregate possible CRISPR/Cas9 off-targets. As previously reported, after 3 generations of backcrosses between heterozygous Galns$^{+/-}$ rats and wild-type rats, almost 99% of possible off-targets were segregated. Afterwards, the fourth generation (F4) of heterozygous rats were crossed to obtain homozygous Galns$^{-/-}$ rats.

Example 5: Analysis of GALNS Activity in Rat Tissues

GALNS activity levels were analysed in serum samples from MPSIVA rats. Heterozygous rats (Galns$^{+/-}$) showed about 50% of GALNS activity of wild-type rats, whereas homozygous rats (Galns$^{-/-}$) did not show GALNS activity (FIG. 2A). Moreover, MPSIVA rats did not present detectable GALNS activity in peripheral tissues, such as liver, spleen, heart or lung (FIG. 2B).

Example 6: Analysis of Keratan Sulfate (KS) Levels in Serum

Serum samples were collected from MPSIVA rats at different ages to determine KS levels by LC-MS/MS mass spectrometry. A progressive increase in KS levels was detected from one to three month of age in both male (FIG. 3A) and female (FIG. 3B) MPSIVA rats.

Example 7: Body Weight Follow-Up of MPSIVA Rats

Figure 4:
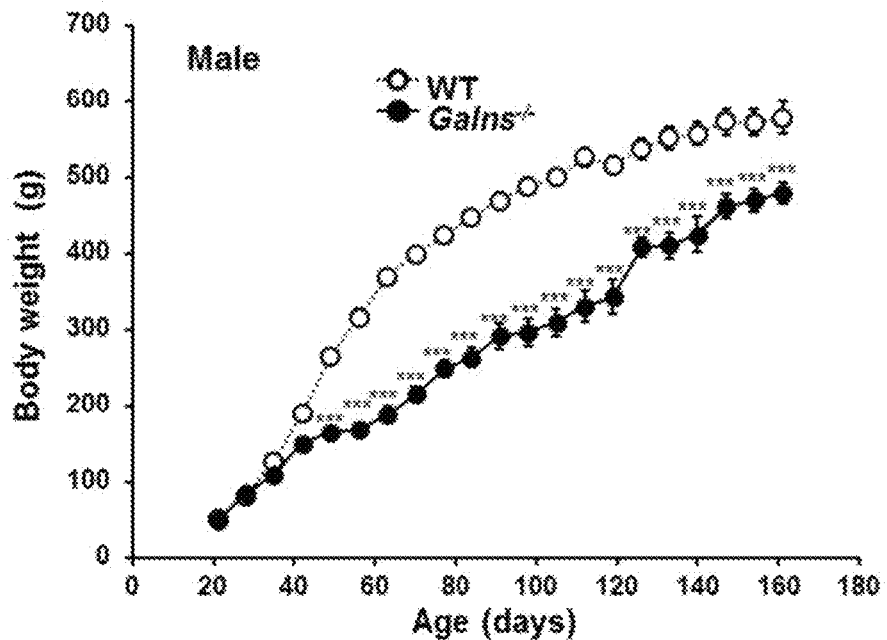
FIG. 4. Body weight of male (A) and female (B) WT and Galns$^{-/-}$ rats. Values are means±SEM of 36-40 animals per group. *P<0.05, ***P<0.001, vs. Galns$^{+/+}$ rats.
Figure 4:
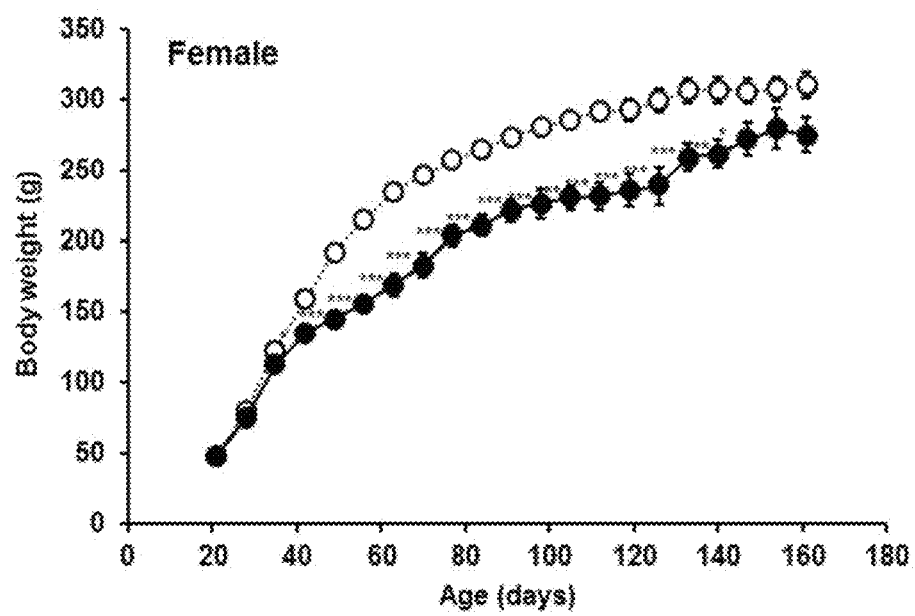
Figure 5:
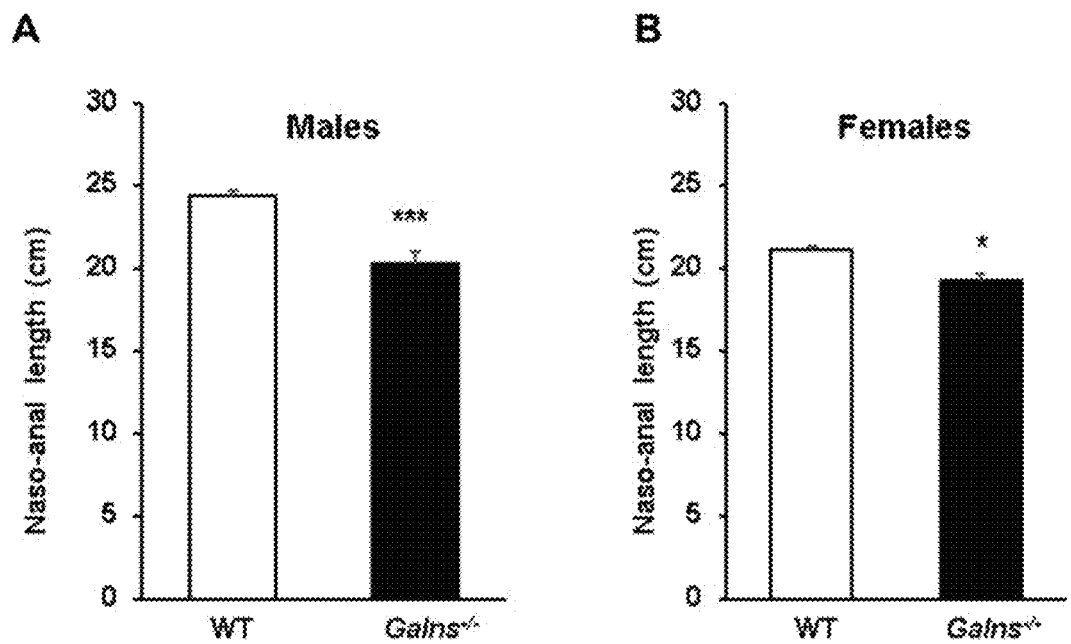
FIG. 5. Measurement of body (nasoanal) length of 3-month-old male (A) and female (B) WT and Galns$^{-/-}$ rats, *P<0.05, ***P<0.001, vs. Galns$^{+/+}$ rats.

Both WT and MPSIVA male and female rats showed similar body weight gain until about 40 days of age. Afterwards, the increase in body weight of MPSIVA rats was lower compared to their wild type counterparts and significant weight differences were observed in both male (FIG. 4A) and female (FIG. 4B) MPSIVA rats. Moreover, at 3 months of age, MPSIVA rats also showed a reduction in body length (naso-anal length) compared with wild-type counterparts (FIG. 5).

Example 8: Analysis of Dental Defects of MPS IVA Rats

Figure 6:
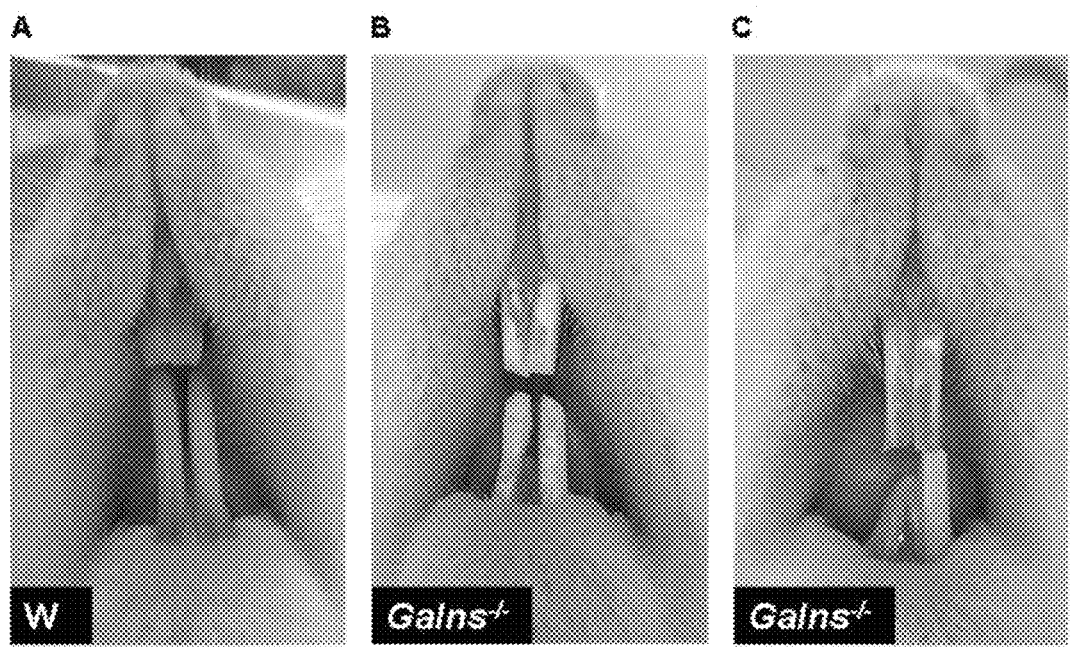
FIG. 6. Representative images of dental alterations observed in 3-month-old Galns$^{-/-}$ rats. (A) WT rat with normal enamel and normal occlusion (B, C) MPSIVA rats showing enamel deficiency, dental fragility and malocclusion.

Morphologic analysis confirmed dental abnormalities in incisors of Galns$^{-/-}$ rats. While WT rats showed normal occlusion and enamel formation (FIG. 6A), 3-month-old MPSIVA rats exhibit enamel deficiency (FIG. 6B), dental fragility (FIG. 6B) and malocclusion (FIG. 6C). In addition, dentine defects were detected in Galns$^{-/-}$ molars, due to an enamel deficiency (FIG. 6A-C). These dental alterations were associated with the loss of GALNS activity and resembled the human MPSIVA dental problems.

Example 9: Micro-Computed Tomography (μCT) Analysis of MPSIVA Rat Bones

Tibia length of WT and MPSIVA rats was analysed by μCT at 3 months of age from medial condyle to medial malleolus. Galns$^{-/-}$ male rats showed a significant reduction in tibia length compared to wild-type male rats (FIG. 7A). Bone alterations were also detected in the jaws of Galns$^{-/-}$ male rats at 3 months of age (FIG. 7B).

Example 10: Morphological and Histological Analysis of MPS IVA Rat Bones

Magnetic resonance imaging (MRI) analysis of the femur and tibia confirmed osteoarthritis signs in 6-month-old MPSIVA male rats. Abnormal presence of synovial fluid was observed inside tibial condyles in sagittal (FIG. 8A) and coronal sections (FIG. 8B). This resulted from the loss of articular cartilage. Osteoarthritis was also analyzed histologically, using haematoxylin-eosin staining of femur and tibia sections. Enlarged chondrocytes and alteration of the articular cartilage were observed in MPSIVA rats (FIG. 8C). These results confirmed that alteration of rat chondrocytes led to abnormal articular cartilage, which finally resulted in osteoarthritis development. Similar alterations are found in human MPSIVA patients (Tomatsu, 2014). Moreover, the alteration in tibial condyles may be consistent with the genu valgum sign, a MPSIVA clinical feature (Tomatsu, 2014).

Example 11: Survival Follow Up of MPS IVA Rats

Figure 9:
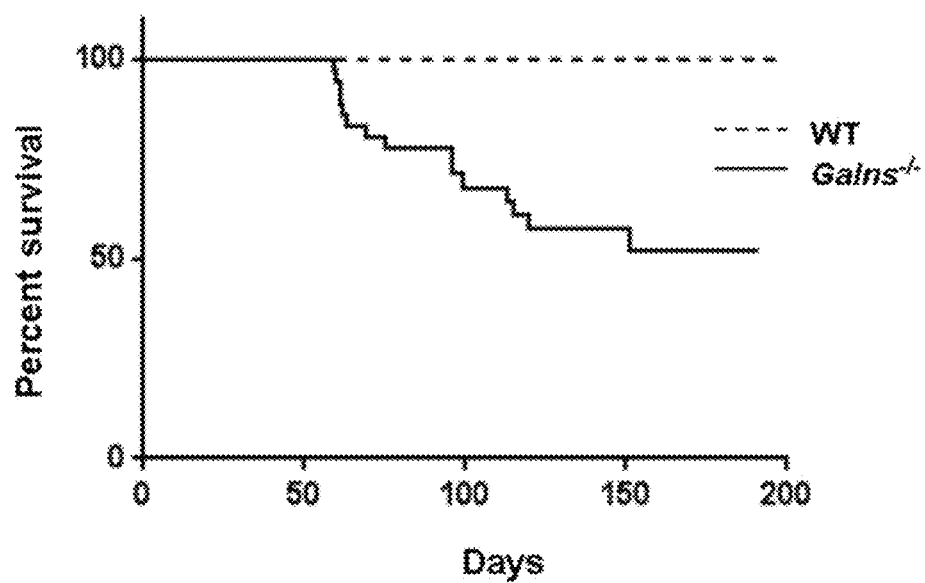
FIG. 9. Survival analysis. Kaplan-Meier analysis of survival in wild-type and Galns$^{-/-}$ male rats. n=15 for WT and n=36 for Galns$^{-/-}$. P=0.013 for Galns$^{-/-}$ vs. WT rats.

Significant differences were observed in the survival curve of MPSIVA compared to wild-type male rats. At 6 months of age, Kaplan-Meier survival analysis showed that 100% of wild type rats were alive, whereas the percentage of living MPSIVA rats was around 50% (FIG. 9).

The invention claimed is:

1. A genetically modified non-human animal model of mucopolysaccharidoses type IVA or Morquio A syndrome comprising a missense mutation in the endogenous Galns gene, wherein said missense mutation is characterized by a substitution of cytosine (C) for thymine (T) at position 1162 (1162 C>T) in a nucleotide sequence as set forth in SEQ ID NO: 3 or a mutation in the amino acid sequence as set forth in SEQ ID NO: 4 consisting of a substitution of arginine (R) for cysteine (C) at position 388 (R388C), wherein said model expresses at least one phenotype associated with mucopolysaccharidoses type IVA or Morquio A syndrome, and wherein the non-human animal model is a rat model.

2. The non-human animal model according to claim 1, wherein said at least one phenotype is dysostosis multiplex.

3. The non-human animal model according to claim 2, wherein said dysostosis multiplex comprises reduced body length and/or bone length compared to wild-type animals.

4. The non-human animal model according to claim 2, wherein said non-human animal model additionally expresses a phenotype selected from osteoarthritis, thin tooth enamel, dental fragility, malocclusion, and combinations thereof.

5. A cell line derived from a non-human animal model according to claim 1.

6. A method for determining the effect of a compound on the animal model according to claim 1, comprising:
   i) placing into contact said animal model with said compound and
   ii) detecting the presence or absence of a physiological, histological or morphological change in said animal as a response to said compound.

7. A method for evaluating the efficacy of a pharmaceutical composition or compound, said method comprising the steps of
   i) providing the non-human animal model of claim 1; and
   ii) evaluating the effect on said non-human animal model of a treatment with said pharmaceutical composition or compound.

8. A method for evaluating the effect of a treatment of mucopolysaccharidoses type IVA or Morquio A syndrome, said method comprising the steps of
   i) providing the non-human animal model of claim 1 with a pharmaceutical composition or compound to be tested,
   ii) evaluating the effect observed on said model treated with a pharmaceutical composition or compound.

* * * * *

```
                        SEQUENCE LISTING

<160> NUMBER OF SEQ ID NOS: 11

<210> SEQ ID NO 1
    <211> LENGTH: 1569
    <212> TYPE: DNA
    <213> ORGANISM: Homo sapiens
    <220> FEATURE:
    <221> NAME/KEY: mutation
    <222> LOCATION: (1156)..(1156)
    <223> OTHER INFORMATION: cytosine at position 1156 is substituted by
          thymine (1156C>T)

<400> SEQUENCE: 1
atggcggcgg ttgtcgcggc gacgaggtgg tggcagctgt tgctggtgct cagcgccgcg      60
gggatggggg cctcgggcgc cccgcagccc cccaacatcc tgctcctgct catggacgac     120
atgggatggg gtgacctcgg ggtgtatgga gagccctcca gagagacccc gaatttggac     180
cggatggctg cagaagggct gcttttccca aacttctatt ctgccaaccc tctgtgctcg     240
ccatcgaggg cggcactgct cacaggacgg ctacccatcc gcaatggctt ctacaccacc     300
aacgcccatg ccagaaacgc ctacacaccg caggagattg tgggcggcat cccagactcg     360
gagcagctcc tgccggagct tctgaagaag gccggctacg tcagcaagat tgtcggcaag     420
tggcatctgg gtcacaggcc ccagttccac cccctgaagc acggatttga tgagtggttt     480
ggatccccca actgccactt tggaccttat gacaacaagg ccaggcccaa catccctgtg     540
tacagggact gggagatggt tggcagatat tatgaagaat ttcctattaa tctgaagacg     600
ggggaagcca acctcaccca gatctacctg caggaagccc tggacttcat taagagacag     660
gcacggcacc acccctttt cctctactgg gctgtcgacg ccacgcacgc acccgtctat     720
gcctccaaac ccttcttggg caccagtcag cgagggcggt atggagacgc cgtccgggag     780
attgatgaca gcattgggaa gatactggag ctcctccaag acctgcacgt cgcggacaac     840
accttcgtct tcttcacgtc ggacaacggc gctgccctca tttccgcccc cgaacaaggt     900
ggcagcaacg gccccttct gtgtgggaag cagaccacgt ttgaaggagg gatgagggag     960
```

-continued

```
cctgccctcg catggtggcc agggcacgtc actgcaggcc aggtgagcca ccagctgggc    1020
agcatcatgg acctcttcac caccagcctg gccttgcgg gcctgacgcc gcccagcgac     1080
agggccattg atggcctcaa cctcctcccc accctcctgc agggccggct gatggacagg    1140
cctatcttct attaccgtgg cgacacgctg atggcggcca ccctcgggca gcacaaggct    1200
cacttctgga cctggaccaa ctcctgggag aacttcagac agggcattga tttctgccct    1260
gggcagaacg tttcagggt cacaactcac aatctgaag accacacgaa gctgcccctg     1320
atcttccacc tgggacggga cccagggag aggttccccc tcagctttgc cagcgccgag    1380
taccaggagg ccctcagcag gatcacctcg gtcgtccagc agcaccagga ggccttggtc    1440
cccgcgcagc cccagctcaa cgtgtgcaac tgggcggtca tgaactgggc acctccgggc    1500
tgtgaaaagt tagggaagtg tctgacacct ccagaatcca ttcccaagaa gtgcctctgg    1560
tcccactag                                                           1569
```

<210> SEQ ID NO 2
<211> LENGTH: 522
<212> TYPE: PRT
<213> ORGANISM: Homo sapiens
<220> FEATURE:
<221> NAME/KEY: MUTAGEN
<222> LOCATION: (386)..(386)
<223> OTHER INFORMATION: Arginine at position 386 is substituted by
      Cysteine (R386C)

<400> SEQUENCE: 2

```
Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
                20                  25                  30

Ile Leu Leu Leu Leu Met Asp Asp Met Gly Trp Gly Asp Leu Gly Val
            35                  40                  45

Tyr Gly Glu Pro Ser Arg Glu Thr Pro Asn Leu Asp Arg Met Ala Ala
        50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190

Glu Phe Pro Ile Asn Leu Lys Thr Gly Glu Ala Asn Leu Thr Gln Ile
        195                 200                 205

Tyr Leu Gln Glu Ala Leu Asp Phe Ile Lys Arg Gln Ala Arg His His
    210                 215                 220

Pro Phe Phe Leu Tyr Trp Ala Val Asp Ala Thr His Ala Pro Val Tyr
```

Ala Ser Lys Pro Phe Leu Gly Thr Ser Gln Arg Gly Arg Tyr Gly Asp
225                 230                 235                 240
                        245                 250                 255

Ala Val Arg Glu Ile Asp Asp Ser Ile Gly Lys Ile Leu Glu Leu Leu
                        260                 265                 270

Gln Asp Leu His Val Ala Asp Asn Thr Phe Val Phe Thr Ser Asp
                        275                 280             285

Asn Gly Ala Ala Leu Ile Ser Ala Pro Glu Gln Gly Gly Ser Asn Gly
                        290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                        325                 330                 335

His Gln Leu Gly Ser Ile Met Asp Leu Phe Thr Thr Ser Leu Ala Leu
                        340                 345                 350

Ala Gly Leu Thr Pro Pro Ser Asp Arg Ala Ile Asp Gly Leu Asn Leu
                        355                 360                 365

Leu Pro Thr Leu Leu Gln Gly Arg Leu Met Asp Arg Pro Ile Phe Tyr
370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                        405                 410                 415

Asp Phe Cys Pro Gly Gln Asn Val Ser Gly Val Thr His Asn Leu
                        420                 425                 430

Glu Asp His Thr Lys Leu Pro Leu Ile Phe His Leu Gly Arg Asp Pro
                        435                 440                 445

Gly Glu Arg Phe Pro Leu Ser Phe Ala Ser Ala Glu Tyr Gln Glu Ala
                        450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                        485                 490                 495

Ala Pro Pro Gly Cys Glu Lys Leu Gly Lys Cys Leu Thr Pro Pro Glu
                        500                 505                 510

Ser Ile Pro Lys Lys Cys Leu Trp Ser His
                        515                 520

<210> SEQ ID NO 3
<211> LENGTH: 1575
<212> TYPE: DNA
<213> ORGANISM: Rattus norvegicus
<220> FEATURE:
<221> NAME/KEY: mutation
<222> LOCATION: (1162)..(1162)
<223> OTHER INFORMATION: cytosine at position 1162 is substituted by
      thymine (1162C>T)

<400> SEQUENCE: 3
atgacggcct gttccacagc gatcagggcc cagcagctac tgctgccggt actgagtgct      60
ctaggactct tggctgcagg tgctccgcag ccccccaaca ttgtgctact gctcatggac     120
gatatggggt ggggtgacct gggtgtgtat ggagaacctt ccagagagac cccaaattta     180
gaccggatgg ctgcagaagg gatgcttttc ccaagcttct attctgccaa ccctttgtgc     240
tcaccatcta gggcagccct gctcacagga cggttgccca tccgcaatgg cttctacaca     300

```
accaacgcac atgcaaggaa tgcttacaca cctcaggaga tcatgggcgg gatccctaac    360
tcagaacacc tcctgcctga gctcctgaag aaagcaggct ataccaacaa gatcgtgggc    420
aaatggcatc tgggtcatag accccagttc caccccctga agcatggatt tgatgagtgg    480
tttggatccc ccaattgtca ttttggacca tacgacaaca aggtcaagcc caacatccct    540
gtgtacaggg actgggaaat ggttggcaga ttttatgaag agttcccaat caacctaaag    600
accggggaag ctaacctcac ccaactctac ttacaagaag ctctggactt catccggaca    660
caacatgcaa ggcagagccc cttcttcctc tactgggcca tcgacgccac acacgcacca    720
gtgtatgcct caaacagtt cctgggtacc agccttcgag ggcgttatgg cgatgctgtc    780
cgggaaatag atgacagtgt tggaaagatc ctgagccttc tgcagaactt gggcatcagt    840
aagaacacat ttgtcttctt tacgtctgac aatggtgcag cgctcatctc tgctcccaaa    900
gaaggtggca gcaatggtcc cttcctgtgt gggaagcaga ctacgtttga aggcgggatg    960
agggagcctg caatcgcttg gtggccaggg cacattgccg caggccaggt cagccaccag   1020
ctgggaagca tcatggacct cttcaccacc agcctgtccc ttgcaggcct gaagcccccc   1080
agtgacaggg taattgatgg ccttgacctc ctccccacca tgctccaggg ccacatcata   1140
gacaggccca tattttatta ccgtggcaac acactgatgg cagtcactct tggccagtac   1200
aaagcacacc tctggacttg gaccaactcc tgggaggagt tcagacaggg cattgacttc   1260
tgccccgggc agaatgtttc aggagtcaca acccacaccc aggaagagca cacggagcta   1320
cccctgatct tccacctggg acgtgaccca ggggagagat tcccactcag gttcaccagc   1380
aatgagtacc aggatgccct cagcaggacc acccaggtca tccagcaaca ccaaaagtct   1440
ttggtccctg acagccccca gctcaatgtg tgtaaccagg ctgtcatgaa ttgggcgcct   1500
ccaggctgtg aaaaactagg gaagtgtctg acacctcctg agtctgtccc cgagaagtgt   1560
ttctgggccc attag                                                   1575
```

<210> SEQ ID NO 4
<211> LENGTH: 524
<212> TYPE: PRT
<213> ORGANISM: Rattus norvegicus
<220> FEATURE:
<221> NAME/KEY: MUTAGEN
<222> LOCATION: (388)..(388)
<223> OTHER INFORMATION: Arginine at position 388 is substituted by
      Cysteine (R388C)

<400> SEQUENCE: 4

```
Met Thr Ala Cys Ser Thr Ala Ile Arg Ala Gln Gln Leu Leu Leu Pro
1               5                   10                  15

Val Leu Ser Ala Leu Gly Leu Leu Ala Ala Gly Ala Pro Gln Pro Pro
            20                  25                  30

Asn Ile Val Leu Leu Leu Met Asp Asp Met Gly Trp Gly Asp Leu Gly
        35                  40                  45

Val Tyr Gly Glu Pro Ser Arg Glu Thr Pro Asn Leu Asp Arg Met Ala
    50                  55                  60

Ala Glu Gly Met Leu Phe Pro Ser Phe Tyr Ser Ala Asn Pro Leu Cys
65                  70                  75                  80

Ser Pro Ser Arg Ala Ala Leu Leu Thr Gly Arg Leu Pro Ile Arg Asn
                85                  90                  95

Gly Phe Tyr Thr Thr Asn Ala His Ala Arg Asn Ala Tyr Thr Pro Gln
            100                 105                 110

Glu Ile Met Gly Gly Ile Pro Asn Ser Glu His Leu Leu Pro Glu Leu
```

```
                115                 120                 125
Leu Lys Lys Ala Gly Tyr Thr Asn Lys Ile Val Gly Lys Trp His Leu
    130                 135                 140

Gly His Arg Pro Gln Phe His Pro Leu Lys His Gly Phe Asp Glu Trp
145                 150                 155                 160

Phe Gly Ser Pro Asn Cys His Phe Gly Pro Tyr Asp Asn Lys Val Lys
                165                 170                 175

Pro Asn Ile Pro Val Tyr Arg Asp Trp Glu Met Val Gly Arg Phe Tyr
            180                 185                 190

Glu Glu Phe Pro Ile Asn Leu Lys Thr Gly Glu Ala Asn Leu Thr Gln
        195                 200                 205

Leu Tyr Leu Gln Glu Ala Leu Asp Phe Ile Arg Thr Gln His Ala Arg
    210                 215                 220

Gln Ser Pro Phe Phe Leu Tyr Trp Ala Ile Asp Ala Thr His Ala Pro
225                 230                 235                 240

Val Tyr Ala Ser Lys Gln Phe Leu Gly Thr Ser Leu Arg Gly Arg Tyr
                245                 250                 255

Gly Asp Ala Val Arg Glu Ile Asp Asp Ser Val Gly Lys Ile Leu Ser
            260                 265                 270

Leu Leu Gln Asn Leu Gly Ile Ser Lys Asn Thr Phe Val Phe Phe Thr
        275                 280                 285

Ser Asp Asn Gly Ala Ala Leu Ile Ser Ala Pro Lys Glu Gly Gly Ser
    290                 295                 300

Asn Gly Pro Phe Leu Cys Gly Lys Gln Thr Thr Phe Glu Gly Gly Met
305                 310                 315                 320

Arg Glu Pro Ala Ile Ala Trp Trp Pro Gly His Ile Ala Ala Gly Gln
                325                 330                 335

Val Ser His Gln Leu Gly Ser Ile Met Asp Leu Phe Thr Thr Ser Leu
            340                 345                 350

Ser Leu Ala Gly Leu Lys Pro Pro Ser Asp Arg Val Ile Asp Gly Leu
        355                 360                 365

Asp Leu Leu Pro Thr Met Leu Gln Gly His Ile Ile Asp Arg Pro Ile
    370                 375                 380

Phe Tyr Tyr Arg Gly Asn Thr Leu Met Ala Val Thr Leu Gly Gln Tyr
385                 390                 395                 400

Lys Ala His Leu Trp Thr Trp Thr Asn Ser Trp Glu Glu Phe Arg Gln
                405                 410                 415

Gly Ile Asp Phe Cys Pro Gly Gln Asn Val Ser Gly Val Thr Thr His
            420                 425                 430

Thr Gln Glu Glu His Thr Glu Leu Pro Leu Ile Phe His Leu Gly Arg
        435                 440                 445

Asp Pro Gly Glu Arg Phe Pro Leu Arg Phe Thr Ser Asn Glu Tyr Gln
    450                 455                 460

Asp Ala Leu Ser Arg Thr Thr Gln Val Ile Gln Gln His Gln Lys Ser
465                 470                 475                 480

Leu Val Pro Gly Gln Pro Gln Leu Asn Val Cys Asn Gln Ala Val Met
                485                 490                 495

Asn Trp Ala Pro Pro Gly Cys Glu Lys Leu Gly Lys Cys Leu Thr Pro
            500                 505                 510

Pro Glu Ser Val Pro Glu Lys Cys Phe Trp Ala His
        515                 520

<210> SEQ ID NO 5
```

```
<211> LENGTH: 22
<212> TYPE: DNA
<213> ORGANISM: Artificial Sequence
<220> FEATURE:
<223> OTHER INFORMATION: gRNA1 guide

<400> SEQUENCE: 5
cccatatttt attaccgtgg ca                                              22

<210> SEQ ID NO 6
<211> LENGTH: 22
<212> TYPE: DNA
<213> ORGANISM: Artificial Sequence
<220> FEATURE:
<223> OTHER INFORMATION: gRNA2 guide

<400> SEQUENCE: 6
taccgtggca acacactgat gg                                              22

<210> SEQ ID NO 7
<211> LENGTH: 120
<212> TYPE: DNA
<213> ORGANISM: Artificial Sequence
<220> FEATURE:
<223> OTHER INFORMATION: Donor DNA
<220> FEATURE:
<221> NAME/KEY: misc_feature
<222> LOCATION: (1)..(50)
<223> OTHER INFORMATION: Left homology arm
<220> FEATURE:
<221> NAME/KEY: misc_feature
<222> LOCATION: (51)..(84)
<223> OTHER INFORMATION: gRNAs target sequence
<220> FEATURE:
<221> NAME/KEY: mutation
<222> LOCATION: (59)..(59)
<223> OTHER INFORMATION: Single silent mutations generating a new MboII
      restriction site
<220> FEATURE:
<221> NAME/KEY: mutation
<222> LOCATION: (66)..(66)
<223> OTHER INFORMATION: Missense mutation: cytosine (C) at position 66
      is substituted by thymine (T) (66C>T)
<220> FEATURE:
<221> NAME/KEY: misc_feature
<222> LOCATION: (85)..(120)
<223> OTHER INFORMATION: Right homology arm

<400> SEQUENCE: 7
tgtaaacaca cagacttgat ctctactctt tctctcctca acacaacagg cccatcttct     60
attactgtgg caacacactg atggcagtca ctcttggcca gtacaaagca cacctctgga   120

<210> SEQ ID NO 8
<211> LENGTH: 20
<212> TYPE: DNA
<213> ORGANISM: Artificial Sequence
<220> FEATURE:
<223> OTHER INFORMATION: Common forward primer

<400> SEQUENCE: 8
tttgtcagcc ccatttccta                                                 20

<210> SEQ ID NO 9
<211> LENGTH: 20
<212> TYPE: DNA
<213> ORGANISM: Artificial Sequence
<220> FEATURE:
<223> OTHER INFORMATION: Common reverse primer

<400> SEQUENCE: 9
```
tgtggtgtga ccattcacct                                              20

<210> SEQ ID NO 10
<211> LENGTH: 915
<212> TYPE: DNA
<213> ORGANISM: Artificial Sequence
<220> FEATURE:
<223> OTHER INFORMATION: PCR amplicon WT sequence (Galns+/+)

<400> SEQUENCE: 10
tttgtcagcc ccatttccta gggcctggct ttgcctccac agggatgagg gcctgccagg      60
ggatgactca ggtcagttcc tgtagccttg ttgtcacaca taccaggcca gtaggaccca     120
ggacctcatg cgtgctggga aatcaccctc ctgagctgtg caccccaatt ccccctgcc     180 ttttgttctc tgtggcctta gcacatcttt aaagtatcgg gtgatacttt aaagtgggca     240
acttgccact cccagccagg agctccacat gtaaacacac agacttgatc tctactcttt     300
ctctcctcaa cacaacaggc ccatatttta ttaccgtggc aacacactga tggcagtcac     360
tcttggccag tacaaagcac acctctggac ttggaccaac tcctgggagg agttcagaca     420
ggtacaggcc tctgaataca gcttctttgg gagggggcac cactgggagg ccgctggaga     480
actgggttga atctctcagc taccaacaaa ggaggcacca ttttcctcac agcctccctc     540
ccttgtgtgt ccctatgggt cctgcccagt cttagttttc acgtccagat gtctagatgg     600
agatggagat tgggcacatg gctctggaaa attctagggg tgtttgagtg gtaccctgct     660
aggggcaaat attctctcct aggatgcact gccctcatag gtggtcttca gagagcgcaa     720
ggtccaggtt caggcagagg gcctctctac ccaccatacc cctaaggctc cacttagcac     780
tcttctcttg ctccctccag gctggcagca tcaggggtgg cctgcccagg tccagatgct     840
gccggccaca actgagacat cagtgtctac atcctggtgc ctgctcaagg ccagaaggtg     900
aatggtcaca ccaca                                                     915

<210> SEQ ID NO 11
<211> LENGTH: 915
<212> TYPE: DNA
<213> ORGANISM: Artificial Sequence
<220> FEATURE:
<223> OTHER INFORMATION: PCR amplicon Galns-/-

<400> SEQUENCE: 11
tttgtcagcc ccatttccta gggcctggct ttgcctccac agggatgagg gcctgccagg      60
ggatgactca ggtcagttcc tgtagccttg ttgtcacaca taccaggcca gtaggaccca     120
ggacctcatg cgtgctggga aatcaccctc ctgagctgtg caccccaatt ccccctgcc     180 ttttgttctc tgtggcctta gcacatcttt aaagtatcgg gtgatacttt aaagtgggca     240
acttgccact cccagccagg agctccacat gtaaacacac agacttgatc tctactcttt     300
ctctcctcaa cacaacaggc ccatcttcta ttactgtggc aacacactga tggcagtcac     360
tcttggccag tacaaagcac acctctggac ttggaccaac tcctgggagg agttcagaca     420
ggtacaggcc tctgaataca gcttctttgg gagggggcac cactgggagg ccgctggaga     480
actgggttga atctctcagc taccaacaaa ggaggcacca ttttcctcac agcctccctc     540
ccttgtgtgt ccctatgggt cctgcccagt cttagttttc acgtccagat gtctagatgg     600
agatggagat tgggcacatg gctctggaaa attctagggg tgtttgagtg gtaccctgct     660
aggggcaaat attctctcct aggatgcact gccctcatag gtggtcttca gagagcgcaa     720

-continued

| | | | | |
|---|---|---|---|---|
| ggtccaggtt | caggcagagg | gcctctctac | ccaccatacc cctaaggctc | cacttagcac | 780 |
| tcttctcttg | ctccctccag | gctggcagca | tcagggtgg cctgcccagg | tccagatgct | 840 |
| gccggccaca | actgagacat | cagtgtctac | atcctggtgc ctgctcaagg | ccagaaggtg | 900 |
| aatggtcaca | ccaca | | | | 915 |